United States Patent [19]
Bachmann et al.

[11] Patent Number: 5,175,108
[45] Date of Patent: Dec. 29, 1992

[54] PLASMIDS FROM CORYNEBACTERIUM GLUTAMICUM AND PLASMID VECTORS DERIVED THEREFROM

[75] Inventors: Frank Bachmann, Moerfelden-Waldorf; Hans J. Kutzner, Oberramstadt; Hans Sonnen, Darmstadt-Arheilgen; Georg Thierbach, Bielefeld; Petra-Sabine Kautz, Bielefeld; Alfred Pühler, Bielefeld; Andreas Schaefer, Bielefeld, all of Fed. Rep. of Germany

[73] Assignee: Degussa Aktiengesellschaft, Frankfurt, Fed. Rep. of Germany

[21] Appl. No.: 750,043

[22] Filed: Aug. 27, 1991

[30] Foreign Application Priority Data

Aug. 30, 1990 [DE] Fed. Rep. of Germany ....... 4027453

[51] Int. Cl.$^5$ .................. C12N 1/21; C12N 15/77
[52] U.S. Cl. .................. 435/252.32; 435/320.1; 435/843
[58] Field of Search .......... 435/69.1, 172.3, 252.3, 435/252.32, 643; 536/27; 935/22, 24, 29, 172

[56] References Cited

PUBLICATIONS

Bourgue et al., Appl. & Environ. Microbiol. 53 (1): 137–141 (1987).
Bourgue et al., Am. J. Vet. Res., 50 (11): 1952–1956 (1989).
Datta et al., J. Bacteriol, 108 (3): 1244–1249 (1971).
Martin et al., Biotechnol., 5: 137–146 (1987).
Yanish-Perron et al., Gene 33: 103–119 (1985).
Oka et al., J. Mol. Biol., 147: 217–226 (1981).
Pridmore, Gene 56: 309–312 (1987).
Simon et al., Biotechnol., 1: 784–791 (1983).

*Primary Examiner*—Richard A. Schwartz
*Assistant Examiner*—Nancy T. Vogel
*Attorney, Agent, or Firm*—Cushman, Darby & Cushman

[57] ABSTRACT

The present invention relates to new plasmids isolated from Corynebacterium glutamicum, plasmid pGA1 and pGA2, which are compatible with one another. In addition, the present invention relates to recombinant plasmids and to plasmid vectors (shuttle vectors) containing the new plasmids. The plasmids and plasmid vectors of the present invention are suitable for use with genetic engineering to improve bacteria strains.

9 Claims, 5 Drawing Sheets

PLASMIDS FROM CORYNEBACTERIUM GLUTAMICUM AND PLASMID VECTORS DERIVED THEREFROM

BACKGROUND OF THE INVENTION

1. Field of the Invention

The present invention relates to new plasmids from *Corynebacterium glutamicum* which are compatible with one another and to plasmid vectors (shuttle vectors) derived therefrom.

2. Background Information

Plasmid vectors are an essential prerequisite for improving bacterial strains by means of genetic engineering. The construction of plasmid vectors for Corynebacterium and Brevibacterium is based, in general, on cryptic plasmids which can be found in this group of bacteria.

Plasmid vectors for Corynebacterium and Brevibacterium can be used to clone genes involved in biosynthesis of amino acids, to express the corresponding gene product or enzyme to an increased degree and to improve the excretion of amino acids therewith. For example, the separation of L-lysine by means of *Corynebacterium glutamicum* can be improved by the cloning and overexpression of the phosphoenol pyruvate carboxylase gene of *Corynebacterium glutamicum* (European patent application No. 89 114 632.6).

Plasmids occur only very infrequently in the group of coryneform bacteria which excrete amino acids, even if the opposite impression might arise upon surveying the literature. As it turns out, upon closer examination, many plasmids described under different names exhibit so many identical qualities that they are to be considered as identical.

Examples of such plasmids are pAM286 from *C. glutamic* AJ11560 (EP-A-0 77 548); pAM330 from *B. lactofermentum* ATCC13869 (EP-A-0 77 548); pBL1 from *B. lactofermenum* ATCC21798 [Santamaria, R. et al., J. Gen. Microbiol. 130, pp. 2237–2246 (1984)] and pX18 from *B. lactofermentum* ATCC21086 [Yeh, P. et al., Gene 47, pp. 301–308(1986)].

The same holds true for the plasmids pHM1519 from *C. glutamicum* ATCC13058 (EP-A-0 78 537), pCG1 from *C. glutamicum* ATCC31808 (EP-A-0 58 889), pRN 3.1 from *C. glutamicum* ATCC39269 (DE-A-3402876) and pSR1 [Yoshihama, M. et al., J. Bact. 162, pp. 591–597 (1985)] from *C. glutamicum* ATCC19223. The high coincidence of the data published about these particular plasmids also shows that identical plasmid species must be involved. Martin, J. F. et al., [Bio/Technology 5, pp. 137–146 (1987)] confirm this assumption.

However, the number of publications and patent applications on this topic shows that there is much interest in a multiplicity of plasmids which are suitable for developing cloning systems for coryneform bacteria.

Plasmids which can exist in a cell adjacent to one another are of particular significance for the development of strains which excrete, for example, amino acids. Such compatible plasmids permit the simultaneous introduction of combinations of biosynthetic genes in a microorganism. Using compatible plasmids the desired enzyme activities can be increased and, in this manner, the formation of the desired product such as, for example, L-threonine or L-lysine can be improved. In particular, it would be especially advantageous to use compatible plasmids one of which exhibits a high copy number and the other a low copy number, in order to achieve a balanced overexpression of the particular genes while avoiding any unnecessary strain on the host.

While compatibility is important, at the same time, the stability of the plasmids used must, of course, be sufficient. As is known from the literature, however, there are no compatibility studies (Martin, J. F. et al., loc. cit., p. 139) or any investigations regarding the stability of plasmid vectors.

SUMMARY OF THE INVENTION

Accordingly, the present invention addresses the problem of making available plasmids and plasmid vectors which are compatible and exhibit sufficient stability to improve the methodological prerequisites for strain improvement by means of genetic engineering.

In particular, it is one object of the present invention provides a means of improving the amino acid excretion of coryneform bacteria, which is beyond the state of the art.

Further objects and advantages of the present invention will be clear from the description that follows.

In one embodiment, the present invention relates to a plasmid pGA1, isolated from *Corynebacterium glutamicum* LP-6 (deposited under number DSM 5816 on 1990-03-02 at Deutsche Sammlung von Mikroorganismen Mascheroder Weg 1 B, W-3300 Braunschweig, characterized by a length of ~4.9 kb and the given restriction cleavage sites.

In another embodiment, the present invention relates to a plasmid pGA2, isolated from *Corynebacterium glutamicum* LP-6 (deposited under number DSM 5816) on 1990-03-02 at Deutsche Sammlung von Mikroorganismen Mascheroder Weg 1 B, W-3300 Braunschweig, characterized by a length of ~19.5 kb and the given restriction cleavage sites.

In a further embodiment, the present invention relates to a recombinant plasmid capable of autonomic replication in coryneform bacteria, comprising plasmid pGA1 or plasmid pGA2 and at least one foreign DNA fragment. The present invention also relates to coryneform bacteria containing the recombinant plasmid.

DETAILED DESCRIPTION OF THE INVENTION

The present invention relates to the plasmid pGA1, isolated from *Corynebacterium glutamicum* LP-6, and deposited under the number DSM 5816. Plasmid pGA1 is characterized by a length of ~4.9 kb and the following restriction cleavage sites:

TABLE 1

| Restriction Enzymes | Number of Cleavage Sites | DNA Fragments (kb) |
|---|---|---|
| Apa I | 0 | — |
| Bam H 1 | 2 | 3,3 1,6 |
| Bcl I | 0 | — |
| Bgl I | 0 | — |
| Bgl II | 0 | — |
| Bst E II | 1 | 4,9 |
| Cla I | 1 | 4,9 |
| Dra I | 0 | — |
| Eco R I | 1 | 4,9 |
| Eco R V | 0 | — |
| Hind III | 4 | 2,4 1,1 1,05 0,3 |
| Kpn I | 0 | — |
| Mlu I | 3 | 2,45 2,25 0,2 |
| Pvu II | 2 | 3,25 1,65 |
| Sal I | 0 | — |
| Sph I | 1 | 4,9 |
| Sst I | 0 | — |
| Xba I | 2 | 2,5 2,4 |
| Xho I | 0 | — |

Figure 1:
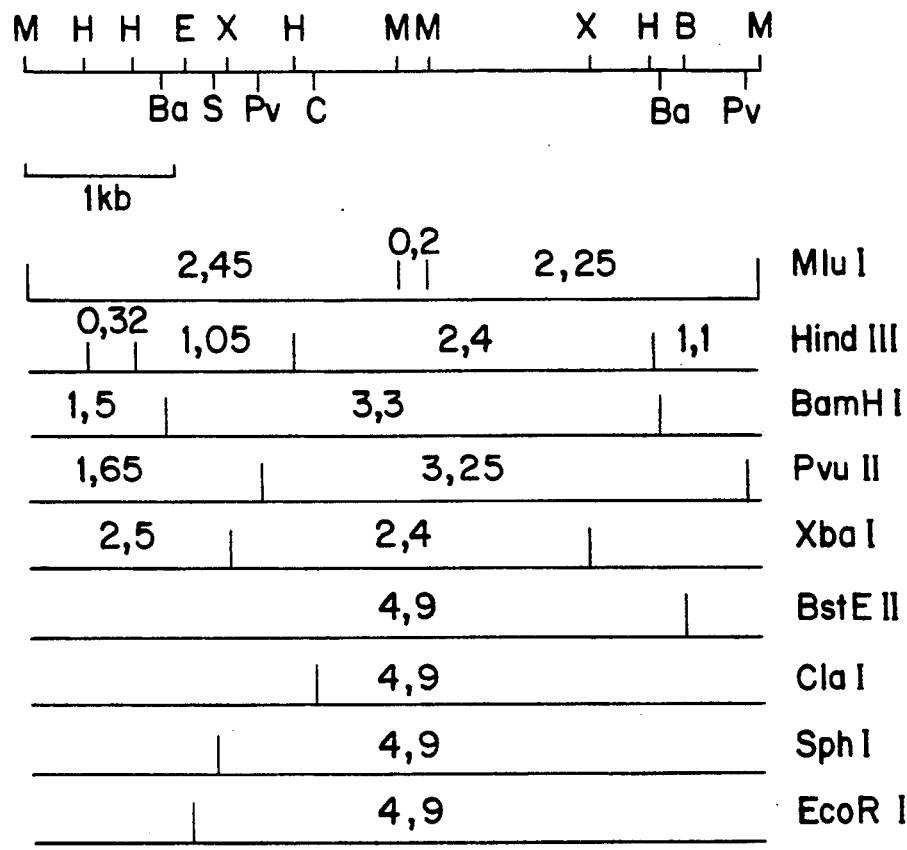
FIG. 1 shows a restriction map of plasmid pGA1 in a linear representation. Abbreviations: Ba, BamHI; B, BstEII; C, ClaI; E, EcoRI; H, HindIII; M, MluI; Pv, PvuII; S, SphI; X, XbaI.

The restriction map of pGA1 in a linear representation is given in FIG. 1.

*Corynebacterium glutamicum* strain LP-6 was obtained from the "Felix d'Herelle Reference Center for Bacterial Viruses" in Quebec 10, Quebec Laval University, Canada G1K 7P4 under number HER1229. The *C. glutamicum* strain LP-6 was deposited in the German Collection of Microorganisms in Braunschweig, Federal Republic of Germany in accordance with the Treaty of Budapest as DSM 5816.

The present invention further relates to plasmid pGA2, which is compatible with pGA1 and is isolated from *Corynebacterium glutamicum* LP-6. Plasmid pGA2 was deposited under the number DSM 5816 and is characterized by a length of ~19.5 kb and the following restriction cleavage sites:

TABLE 2

| Restriction Enzymes | Number of Cleavage Sites | DNA Fragments (kb) |
|---|---|---|
| Bam H I | 3 | 13,6 4,15 1,75 |
| Eco R I | 2 | 18,5 0,96 |
| Hind III | 5 | 6,61 5,72 3,31 2,04 1,82 |
| Hpa I | 1 | 19,5 |
| Kpn I | 1 | 19,5 |
| Mlu I | 3 | 15,8 2,84 0,82 |
| Sca I | 1 | 19,5 |
| Sma I | 4 | 14,5 3,34 1,00 0,65 |
| Xho I | 0 | — |

Figure 2:
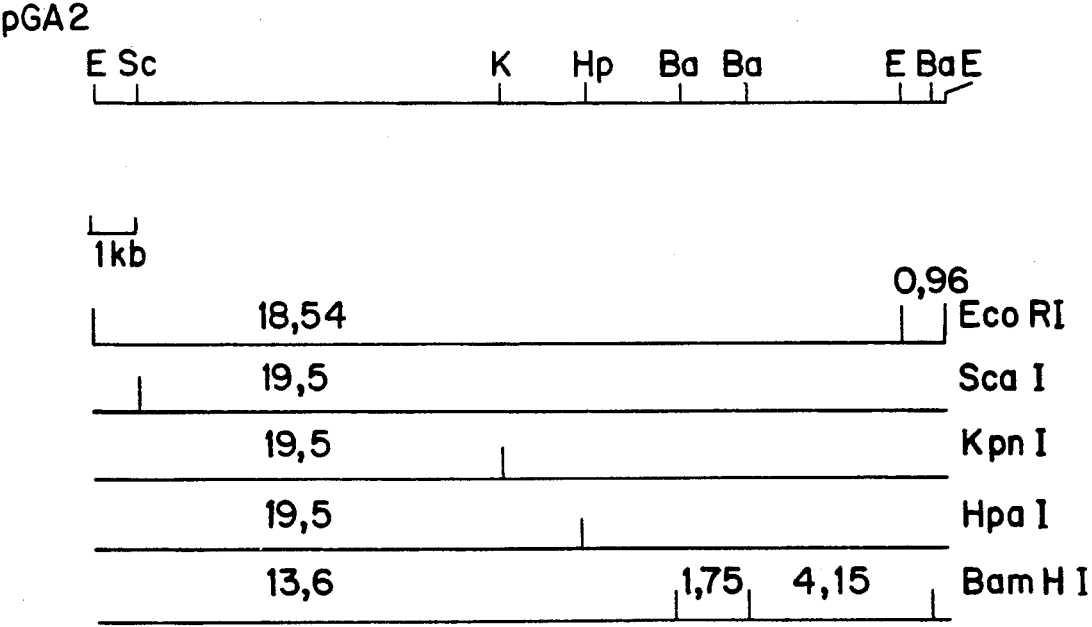
FIG. 2 shows a restriction map of plasmid pGA2 in a linear representation. Abbreviations: Ba, BamHI; E, EcoRI; Hp, HpaI; K, KpnI; Sc, ScaI.

FIG. 2 shows the restriction map of pGA2 in a linear representation.

Plasmids pGA1 and pGA2 are compatible. Moreover, whereas plasmid pGA1 exhibits a high copy number (~50 per cell), a lower copy number (~5 per cell) occurs with pGA2.

The plasmid DNA can be isolated from the deposited strains in accordance with methods well known in the art.

Coryneform bacteria, especially bacteria which produce amino acids, are suitable as host for the plasmids of the present invention. Examples of such coryneform bacteria are:

*Brevibacterium flavum*, (especially ATCC 14067); *Brevibacterium lactofermentum*, (especially ATCC 13869); *Corynebacterium callunae*, (especially ATCC 15991) *Corynebacterium Glutamicum*, (especially ATCC 13032); *Corynebacterium melassecola*, (especially ATCC 17965); and *Corynebacterium thermoaminogenes*, (especially Ferm P-9244).

Since the plasmids of the present invention multiply in the cells of coryneform bacteria, they are capable of amplifying the information of foreign genes they contain within the host cells.

The insertion of the recombinant plasmid DNA into the host cells preferably takes place via plasmids cloning vectors. Vectors especially suitable for use comprise a resistance gene and replicate in *E. coli*, such as, for example, pACYC177, pACYC184, pSC101, pBR322, pIP55, R16, R1, RP4 and pIE545.

The principle of such constructions is described in EP-A-93611 and EP-A-82485.

Figure 4:
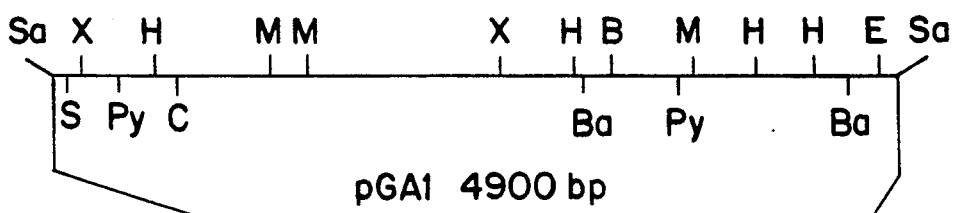
FIG. 4 shows a restriction map of plasmid pHS2-1 in a linear representation. The pGA1- and the pHSKm1 part 1 are represented separately. The pGA1 part of pHS2-1 contains at least 6 HaeII restriction cleavage sites which were not sketched in. Abbreviations: Sa, Sau3A; all other abbreviations are explained in FIG. 1.
Figure 4:
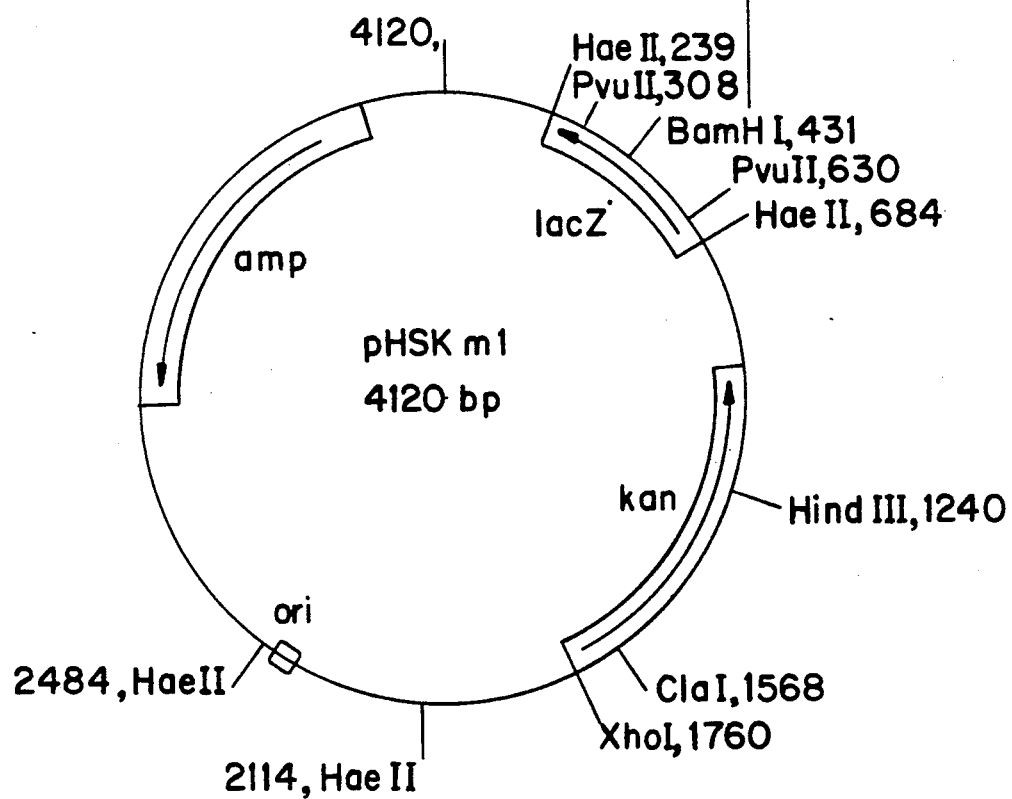

One preferred vector is the shuttle vector pHS 2-1, consisting of the plasmid pGA1 and the *E. coli* vector pHSKm1, which is characterized by the restriction map given in FIG. 4. The vector pHSKm1 is a derivative of the *E. coli* vector pUC18, [which is described in Yanish-Perron, C. et al., Gene 33, pp. 103-119 (1985)] into which the kanamycin resistance gene of transposon Tn 903 was inserted. This and other shuttle vectors based on pGA1 are not only stable in coryneform bacteria, especially *Corynebacterium glutamicum*, but also coexist with plasmids of other origin, such as, for example, pHM1519 from *Corynebacterium glutamicum* ATCC 13058 and pAM 330 from *Brevibacterium lactofermentum* ATCC 13869, and especially with pCC1 from *Coryebacterium callunae* DSM 20147. This is surprising because a plasmid or a vector with a high copy number is involved in the cited instances.

*Brevibacterium lactofermentum* ATCC 13869, which carries the plasmid pAM 330, was transformed with pHS2-1 DNA as described in Thierbach et al., [Appl. Microbiol. Biotechnol. 29, pp. 356-362 (1988)]. An investigation of the transformants showed that both plasmids coexisted.

A mobilizable derivative of plasmid pGA1 was introduced into *Corynebacterium glutamicum* ATCC13058, which carries the plasmid pHM1519, with the aid of the conjugation method as in Schäfer et al., [J. Bact. 172, pp. 1663-1666 (1990)]. Again an investigation of the transconjugants showed that both plasmids can coexisted.

Plasmid pGA2 is also suitable for the construction of mobilizable shuttle vectors. The shuttle vector pFBH2, which replicates in *Corynebacterium glutamicum*, is constructed from a DNA sequence of pGA2 and the mobilizable *E. coli* vector pk18::mob.

EXAMPLES

The following non-limiting examples are given to further describe the present invention.

1. Isolation and Characterization of pGA1 from *Corynebacterium glutamicum* LP-6

*Corynebacterium glutamicum* strain LP-6 was obtained from the "Felix d'Herelle Reference Center for Bacterial Viruses" in Quebec 3 10, Quebec Laval University, Canada G1K 7P4 under number HER1229. The *C. glutamicum* strain LP-6 was deposited in the German Collection of Microorganisms in Braunschweig, Federal Republic of Germany in accordance with the Treaty of Budapest as DSM5816.

Plasmid DNA was isolated from strain LP-6 in accordance with methods known in the art such as those described, for example, in European patent application 0 318 663 and in Birnboim, H. C. and Doly, J. [Nucleic Acids Research 7, pp. 1513-1523 (1979)]. The DNA solution obtained in this manner was characterized by means of agarose gel electrophoresis (Maniatis, T. et al. (1982), Molecular Cloning: A Laboratory Manual, Cold Spring Harbor). The DNA solution contained two plasmid species which were characterized as pGA1 and pGA2. Plasmid pGA1 had a length of approximately 4.9 kb and plasmid pGA2 had a length of approximately 19.5 kb. Plasmid pGA2 was cleaved with restriction enzyme SalI whereas pGA1 remained intact.

The DNA solution obtained in this manner was subjected to a CsCl/ethidium-bromide density gradient centrifugation (Maniatis, t. et al. (1982), Molecular Cloning: A Laboratory Manual, Cold Spring Harbor) and the plasmid pGA1 isolated therefrom.

Plasmid pGA1 was treated with the restriction enzymes ApaI, BamHI, BclI, BglI, BglII, BstEII, ClaI, DraI, EcoRI, EcoRV, HindIII, KpnI, MluI, PvuII, SalI, SphI, SstI, XbaI and XhoI. The length of the DNA fragments was determined by means of agarose gel electrophoresis and length comparison with standard known DNA fragments. Such a standard is, for example, DNA of the *Escherichia coli* phage, which is cleaved with the restriction enzyme HindIII and can be obtained from the firm Bethesda Research Laboratories in Gaithersburg, Md., USA Table 1 indicates the number of restriction cleavage sites in plasmid pGA1 for the restriction enzymes investigated and the length of the DNA fragments obtained. The restriction map of the plasmid, shown in FIG. 1, was established by digesting pGA1 with two and three restriction enzymes and determinating of length of the DNA fragments obtained. Plasmid pGA1 has a length of approximately 4.9 kb.

The copy number of pGA1 in strain LP-6 was determined in the following manner. Strain LP-6 was cultivated in standard I broth (obtained from the firm Merck, Darmstadt, Federal Republic of Germany) until the start of the stationary growth phase and the cell number determined. The plasmid DNA was isolated from 1.5 ml culture suspension as described in Birnboim, H. C. and Doly, J. [Nuclear Acids Research 7, pp. 1513-1523 (1979)]. An aliquot of the plasmid DNA solution and a known amount of the above-described HindIII DNA standard were subjected to an agarose gel electrophoresis with subsequent ethidium bromide staining. The fluorescence under UV irradiation of the pGA1 DNA bands was compared to that of the HindIII DNA fragments and the amount of pGA1 DNA determined semi-quantitatively in this manner. The copy number (number of plasmid molecules per cell) was determined as approximately 50 in this manner.

2. Isolation and characterization of pGA2 from *Corynebacterium glutamicum* LP-6

A solution containing plasmid DNA with the plasmids pGA1 and pGA2 was prepared as described above in Example 1. The two plasmid species were separated by means of agarose gel electrophoresis and plasmid pGA2 isolated by means of electroelution (Maniatis, T. et al. (1982), Molecular Cloning: A Laboratory Manual, Cold Spring Harbor).

Plasmid pGA2 was treated with the restriction enzymes EcoRI, BamHI, KpnI, ScaI, HpaI, MluI, SmaI, HindIII and XhoI. The length of the DNA fragments was determined as described above in Example 1. Table 2 shows the number of restriction cleavage sites in plasmid pGA2 for the restriction enzymes investigated and the length of the DNA fragments obtained. A restriction map of the plasmid, shown in FIG. 2, was established from the digestion of pGA2 with two and three restriction enzymes and determination of length of the DNA fragments obtained. Plasmid pGA2 has a length of approximately 19.5 kb.

The copy number of pGA2 in strain LP-6 was determined in the following manner. Strain LP-6 was cultivated in standard I broth (obtained from the firm Merck, Darmstadt, Federal Republic of Germany) until the start of the stationary growth phase and the cell number determined. The plasmid DNA was isolated from 1.5 ml culture suspension as described in Birnboim, H. C. and Doly, J. [Nuclear Acids Research 7, pp. 1513-1523 (1979)]. An aliquot of the plasmid DNA solution and a known amount of the above-described HindIII DNA standard were subjected to an agarose gel electrophoresis with subsequent ethidium bromide staining. The fluorescence under UV irradiation of the pGA2 DNA bands was compared to that of the HindIII DNA fragments and the amount of pGA2 DNA determined semi-quantitatively in this manner. The copy number (number of plasmid molecules per cell) was determined as approximately 5 in this manner.

TABLE 2

| Characterization of plasmid pGA2 by means of restriction endonucleases | | | | |
|---|---|---|---|---|
| Restriction Enzymes | Number of Cleavage Sites | DNA Fragments (kb) | | |
| BamHI | 3 | 13,6 | 4,15 | 1,75 |
| EcoRI | 2 | 18,5 | 0,96 | |
| Hind III | 5 | 6,61 | 5,72 | 3,31 |
|  |  | 2,04 | 1,82 | |
| HpaI | 1 | 19,5 | | |
| KpnI | 1 | 19,5 | | |
| MluI | 3 | 15,8 | 2,84 | 0,82 |
| ScaI | 1 | 19,5 | | |
| SmaI | 4 | 14,5 | 3,34 | 1,00 |
|  |  | 0,65 | | |

TABLE 2-continued

| Characterization of plasmid pGA2 by means of restriction endonucleases | | |
|---|---|---|
| Restriction Enzymes | Number of Cleavage Sites | DNA Fragments (kb) |
| XhoI | 0 | — |

3. Construction of the shuttle vector pHS2-1 consisting of pGA1 and the *Escherichia coli* vector pHSKm1

Plasmid pHSKm1 is a derivative of the *E. coli* vector pUC18, described in Yanisch-Perron, C. et al. [Gene 33, pp. 103–119 (1985)] and obtainable from the firm Pharmacia in Uppsala, Sweden, into which the kanamycin resistance gene of transposon Tn903 [Oka, A. et al., J. Mol. Biol. 147, pp. 217–226 (1981)] was inserted.

Plasmid pHSKm1 was constructed as follows. Plasmid pACYC177, which carries the kanamycin resistance gene of transposon Tn903 [Rose, R. E.; Nucleic Acids Research 16, p. 356 (1988)], was isolated from *Escherichia coli* ATCC37031 in the manner described in EPA 0 318 663. Plasmid pACYC177 was split with restriction enzyme HaeII and the DNA fragment with a length of 1430 bp, which carries the kanamycin resistance gene, was isolated by means of electroelution (Maniatis, T. et al. (1982), Molecular Cloning: A Laboratory Manual. Cold Spring Harbor). Plasmid pUC18 was partially split with HaeII, mixed with the HaeII DNA fragment 1430 bp in length and the resulting DNA mixture treated with T4-DNA ligase. Competent cells of *Eschercha coli* DH5α, which were obtained from the firm Bethesda Research Laboratories in Gaithersburg, Md., USA, were transformed with the ligation mixture.

Figure 3:
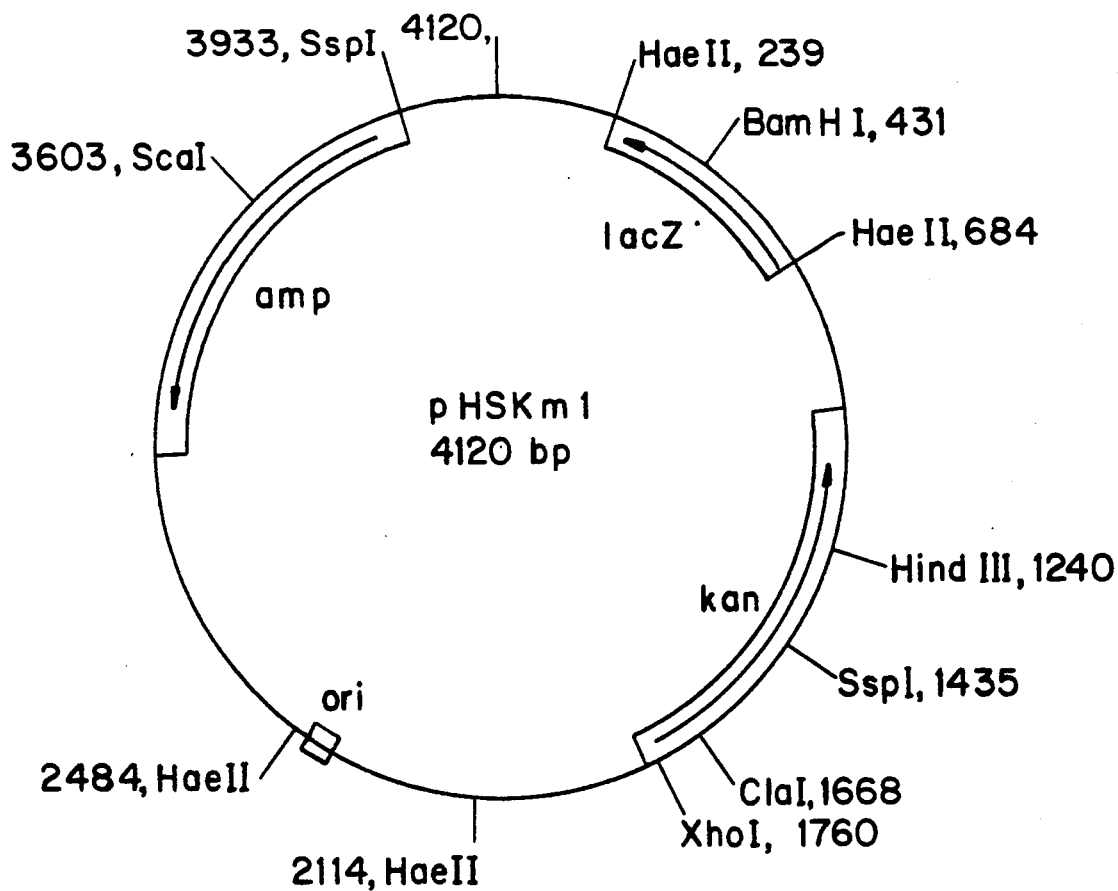
FIG. 3 shows a restriction map of plasmid pHSKm1 in a circular representation. The multiple cloning site extends between positions 400 to 452. Abbreviations: amp, ampicillin resistance gene; Kan, kanamycin resistance gene; lacZ', 5'-terminal part of the lacZ gene which permits lacZα complementation; ori, origin of replication.

Kanamycin-resistent transformants were selected on LB agar (tryptone: 10 g/l yeast extract: 5 g/l; NaCl: 10 g/l; agar: 12 g/l) which had been supplemented with 20 μg/ml kanamycin. The plasmid designated as pHSKm1 was isolated from a transformant. The position and orientation of the inserted DNA fragment 1430 bp long with the kanamycin resistance gene was determined by means of restriction analysis. FIG. 3 shows the restriction map of plasmid pHSKm1.

Plasmid pGA1, which was described above in Example 1 was partially digested with restriction enzyme Sau3A and the linearized form of the plasmid, which was cut once, isolated by electroelution. The DNA obtained in this manner was mixed with pHSKm1 DNA which had been linearized with BamHI and the resulting DNA mixture treated with T4 DNA ligase.

*Escherichia coli* DH5α was transformed with the ligation mixture and transformants selected on LB agar which had been supplemented with kanamycin (20 μg/ml), X-gal (5-bromo-4-chloro-3-indolyl-D-galactopyranoside, 40 μg/ml) and IPTG (isopropyl-β-D-thiogalactopyranoside, 20 μg/ml). Approximately 5% of the transformants were colorless on the described agar.

A colony hybridization with plasmid pGA1 as probe was carried out with approximately 900 transformants which did not exhibit any LacAα complementation. pGA1 was marked for the colony hybridization by means of "nick" translation (Maniatis, T. et al. (1982), Molecular Cloning: A Laboratory Manual, Cold Spring Harbor) with biotinylated nucleoside triphosphates (biotin-7-dATP) and demonstrated with the aid of the BluGENE nucleic acid demonstration system of the firm Bethesda Research Laboratories in Gaithersburg, Md., USA by means of streptavidine-coupled alkaline phosphatase. The marking of the DNA was carried out as described in Langer et al. [Proceedings of the National Academy of Sciences, USA, 80, pp. 6633–6637 (1981)] and the colony hybridization carried out as described in Trevor, G. T. (Microbiological Methods 3, 259 pp. [sic] (1985)). Of the 900 transformants tested, 70 had a positive reaction. The plasmid designated as pHS2-1 was isolated from a transformant and mapped with the aid of restriction enzymes. FIG. 4 shows the restriction map of plasmid pHS2-1.

4. Replication of shuttle vector pHS2-1 in *Corynebacterium glutamicum* ATCC 13032

Plasmid pHS2-1 was isolated from *Escherichia coli* DH5α/pHS2-1 and spheroplasts of *Corynebacterium glutamicum* ATCC13032 were transformed therewith as described in Thierbach et al. [Appl. Microbiol. Biotechnol. 29, pp. 356–362 (1988)]. Transformants were selected on SB agar containing kanamycin (15 μg/ml). Plasmid DNA was isolated from 12 transformants and characterized by means of splitting with the restriction enzymes EcoRI and MluI. The plasmid DNA had the same size and exhibited the same restriction pattern as pHS2-1, isolated from *Escherichia coli*.

5. Stability of shuttle vector pHS2-1 in *Corynebacterium glutamicum* ATCC13032

*Corynebacterium glutamicum* ATCC13032/pHS2-1 was cultivated in standard I nutrient broth (obtained from the firm Merck, Darmstadt, Federal Republic of Germany) which had been supplemented with 4 g/l glucose and additionally with 10 μg/ml kanamycin at 30° C. and 150 rpms until attainment of the stationary growth phase. A 50 ml culture consisting of the above-described nutrient medium with kanamycin and a 50 ml culture consisting of the above-described nutrient medium without kanamycin were each inoculated with the preculture in a ratio of 1:10,000 and cultivated as described above until attainment of the stationary growth phase. The optical density of the bacterial culture was 7 to 8 at a measuring wavelength of 660 nm.

The kanamycin-containing bacterial culture was then transferred in a ratio of 1:10,000 onto fresh kanamycin-containing nutrient broth and the bacterial culture which had grown in the absence of kanamycin was transferred, in the same ratio, onto fresh nutrient broth free of kanamycin. A total of 16 such transfers were carried out, so that the strain was cultivated for approximately 210 generations in the presence of and in the absence of kanamycin. Then, specimens were plated out onto standard I agar (obtained from the firm Merck, Darmstadt, Federal Republic of Germany) and incubated at 30° C. The developing individual colonies were stamped onto standard I agar and onto standard I agar which had been supplemented with 10 μg/ml kanamycin. In the case of the culture for 210 generations in the absence of kanamycin, 181 of 181 individual colonies tested were kanamycin-resistent and in the case of the culture in the presence of kanamycin, 84 of 84 individual colonies tested were kanamycin-resistent. Plasmid DNA was isolated from each of 12 individual colonies and characterized by splitting with the restriction enzymes EcoRI and MluI. The plasmid DNA exhibited the size of pHS2-1 and displayed the restriction pattern characteristic for pHS2-1.

6. Coexistence of the plasmid pCC1 from *Corynebacterium callunae* DSM20147 with shuttle vector pHS2-1

*Corynebacterium callunae* DSM 20147 was transformed with pHS2-1 plasmid DNA, isolated from *Corynebacterium glutamicum* ATCC 13032/pHS2-1, in the manner described in Thierbach et al. [Appl. Microbiol. Biotechnol. 29, pp. 356–362 (1988)]. Transformants were selected on SB agar containing kanamycin (15 μg/ml). 20 transformants were individualized on standard I nutrient agar which had been supplemented with kanamycin (10 μg/ml). Each individual removed and plasmid DNA isolated. Plasmid pCC1 was demonstrated by agarose gel electrophoresis in 17 of 20 individual colonies of the type DSM20147/pHS2-1 tested; plasmid pHS2-1 was present in all clones tested.

Spheroplasts of *Corynebacterium callunae* DSM20147 were produced in the same manner as a control and regenerated on SB agar. 20 regenerated individual colonies were individualized on standard I nutrient agar. Each individual colony was removed and plasmid DNA isolated. Plasmid pCC1 was demonstrated in 17 of 20 individual colonies of the type DSM 20147 tested. A transformant of the type DSM20147/pHS2-1 was cultivated for approximately 50 generations in the presence and in the absence of kanamycin in the manner described above in Example 5. The two cultures were subsequently platted out onto standard I agar and incubated at 30° C. Plasmid DNA was isolated from each of 8 individual colonies. The plasmids pCC1 and pHS2-1 were able to be demonstrated in 8 of 8 colonies tested.

A regenerated individual colony of strain DSM20147 was cultivated in the same manner as the control for approximately 50 generations and subsequently isolated onto the plasmid DNA from 8 individual colonies. Plasmid pCC1 was demonstrated in 8 of 8 individual colonies tested. The investigation showed that plasmids pCC1 and pHS2-1 can coexist.

7. Excretion of L-lysine by *Corynebacterium glutamicum* strain LP-6

Strain LP-6 was cultivated in a medium which consisted of 12 g/l ammonium sulfate, 240 g/l molasses and 60 ml/l soybean meal hydrolysate and whose pH had been adjusted to approximately 7.2 with ammoniacal water. 100 ml Erlenmeyer flasks were filled with 10 ml of the above-described medium, inoculated with strain LP-6 and incubated 72 hours at 30° C. and 300 rpms. The determination of L-lysine took place in the centrifuged supernatant with the aid of amino-acid analyzers. The excreted concentration of L-lysine.HCl was 0.9 g/l.

8. Construction of the mobilizable shuttle vector pFBH2 consisting of a DNA sequence from pGA2 and the mobilizable *Escherichia coli* vector pK18::mob Plasmid pK18::mob is a derivative of the *Escherichia coli* cloning vector pK18, [Pridmore, R. D., Gene 56, pp. 309–312 (1987)]. Plasmid pK18::mob carries the region of the self-transferrable plasmid RP4 essential for mobilization [Datta, N. et al., J. Bact. 108, pp. 1244–1249 (1971)] and was constructed as follows. Plasmid pSUP102, which carries the mobilization region of plasmid RP4[Simon, R. et al., Methods in Enzymology 118, pp. 640–659 (1986)], was isolated from *Escherichia coli* S17-1[Simon, R. et al., Biotechnology 1, pp. 784–794 (1983)] according to known methods, for example, in Holmes, D. S. & Quigley, M. [Analyt. Biochem. 114, pp. 193–197 (1981)] and partially split with the restriction enzyme AluI. Plasmid pK18 was partially digested with the restriction enzyme NaeI, combined with the DNA fragments obtained by means of AluI digestion of plasmid pSUP102 and the resulting DNA mixture treated with T4 DNA ligase. Competent cells of *Escherichia coli* S17-1 which had been produced in accordance with the instructions of Cohen, S. et al. [Proc. Natl. Acad. Sci. USA 69, pp. 2110–2114 (1972)] were transformed with the ligation mixture and the cells placed on PA agar consisting of 17.5 g/l Penassay broth (Difco Laboratories, Detroit, Mich., USA) and 15 g/l agar to which kanamycin with a final concentration of 25 μg/ml had been added. Kanamycin-resistant colonies were rinsed with PA liquid medium, cultivated in a fairly large amount of PA liquid medium and used in accordance with current methods as described in Simon, R. et al. [Biotechnology 1, pp. 784–794 (1983)] for crossing with *Escherichia coli* MM294[Talmadge, K. and Gilbert, W. Gene 12, pp. 235–241 (1980)]. Derivatives of plasmid pK18 which carried the insertions of pSUP102 DNA were able to be isolated from the transconjugants grown on selection medium (PA agar with 25 μg/ml kanamycin and 50 μg/ml nalidixic acid).

Figure 5:
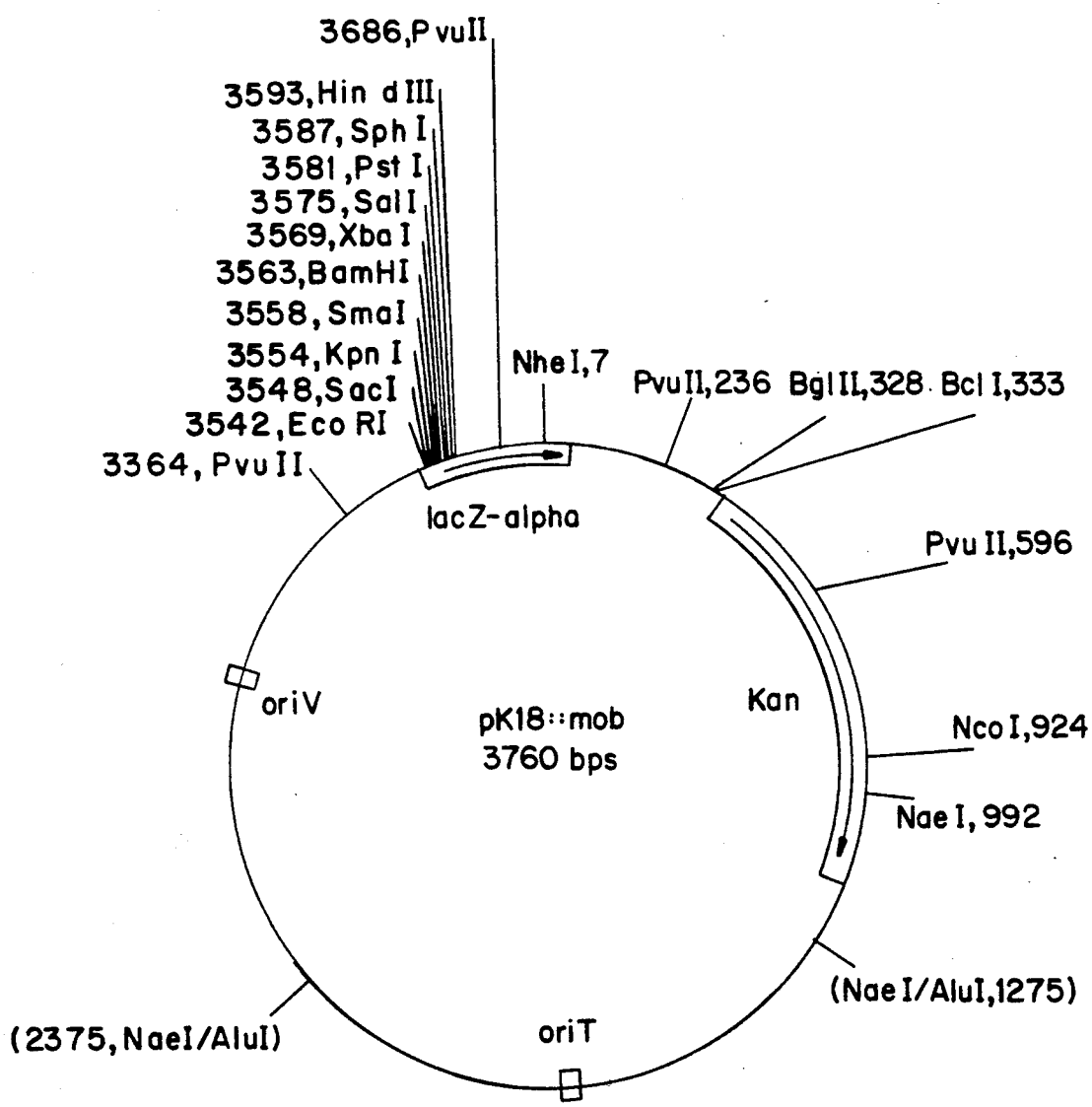
FIG. 5 shows a restriction map of plasmid pK18::mob in a circular representation. Abbreviations: Kan, kanamycin resistance gene; lacZ-alpha, 5'-terminal part of the lacZ gene which permits lacZα complementation; oriV, origin of replication; oriT, origin for the conjugative plasmid transfer (mobilization region). The DNA area between the positions (2375, NaeI/AluI) and (1275, NaeI/AluI) carries 3 NaeI restriction cleavage sites which were not mapped.

The vector designated here as pK18::mob carries a pSUP102 insertion with a length of 1.1 kb. The position of the inserted DNA fragment with the mobilization region was determined by means of restriction analysis. FIG. 5 shows the restriction map of plasmid pK18::mob.

Figure 6:
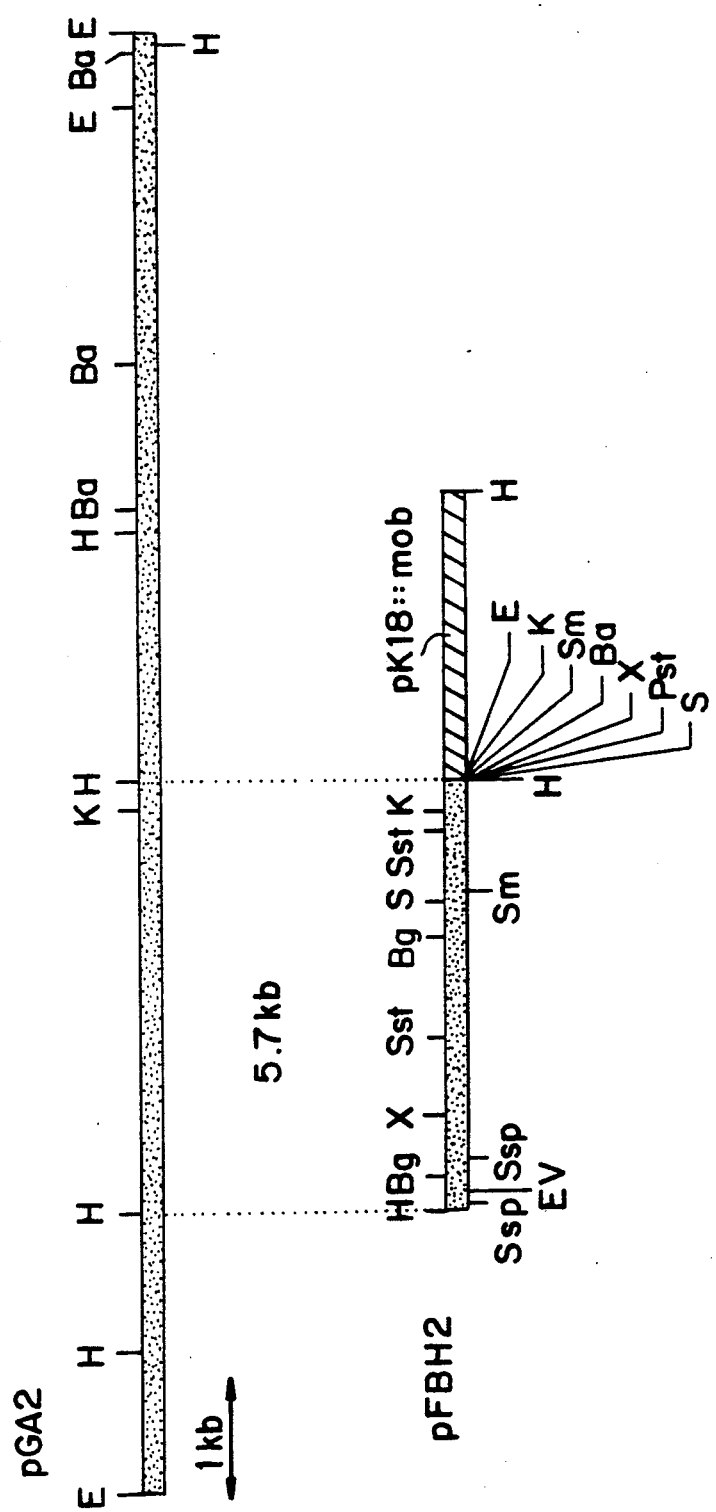
FIG. 6 shows a restriction map of plasmid pFBH2 in a linear representation. Abbreviations: Ba, BamHI; Bg, BglII; E, EcoRI; EV, EcoRV; H, HindIII; K, KpnI; Pst, PstI; Sm, SmaI; S, SphI; Ssp, SspIL; Sst, SstI; X, XbaI. The pGA2 part of the molecule is characterized by gray shading and the pK18::mob part by hatching.

Plasmid pGA2, which is described above in Example 2, was split with the restriction enzyme HindIII and the resulting pGA2 DNA fragments mixed with plasmid vector pK18::mob, which had been previously linearized with HindIII. The resulting DNA mixture was treated with T4 DNA ligase and subsequently used for the transformation of *Escherichia coli* DH5α. Transformants were selected on LB agar which had been supplemented with kanamycin (20 μg/ml), X-gal (40 μg/ml) and IPTG (20 μg/ml). All colorless colonies were checked for plasmid content with plasmid preparations known in the art like those described, for example, in Birnboim, H. C. and Doly, J. [Nucleic Acids Research 7, pp. 1513–1523, (1979)] and the plasmids characterized with the aid of restriction enzymes. One of the isolated plasmids carried a pGA2 insertion with a length of 5.7 kb and was designated as pFBH2. FIG. 6 shows the restriction map of pFBH2.

9. Replication of shuttle vector pFBH2 in *Corynebacterium glutamicum* RM3

*Escherichia coli* S17-1 was transformed with pFBH2 DNA (isolated from DH5α/pFBH2) and the resulting transformants selected on LB agar with kanamycin (20 μg/ml). A transformant of the type S17-1/pFBH2 was used for conjugation with *Corynebacterium glutamicum* RM3 as described in Schäfer et al. [J. Bact. 172, pp. 1663–1666, (1990)]. Transconjugants of *C. glutamicum* RM3 were selected on LB agar which had been supplemented with kanamycin (20 μg/ml) and nalidixic acid (50 μg/ml). Plasmid DNA was isolated from 12 transconjugants and characterized by means of splitting with various restriction enzymes. The isolated plasmid DNA had the same size and exhibited the same restriction pattern as pFBH2, isolated from *Escherichia coli*.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

We claim:

1. A plasmid pGA1, isolated from *Corynebacterium glutamicum* LP-6 (deposited under number DSM 5816) characterized by a length of ~4.9 kb and the following restriction cleavage sites:

| Restriction enzymes | Number of cleavage sites | DNA fragments (kb) |
| --- | --- | --- |
| Apa I | 0 | — |
| Bam H I | 2 | 3,3 1,6 |
| Bcl I | 0 | — |
| Bgl I | 0 | — |
| Bgl II | 0 | — |
| Bst E II | 1 | 4,9 |
| Cla I | 1 | 4,9 |
| Dra I | 0 | — |
| Eco R I | 1 | 4,9 |
| Eco R V | 0 | — |
| Hind III | 4 | 2,4 1,1 1,05 0,3 |
| Kpn I | 0 | — |
| Mlu I | 3 | 2,45 2,25 0,2 |
| Pvu II | 2 | 3,25 1,65 |
| Sal I | 0 | — |
| Sph I | 1 | 4,9 |
| Sst I | 0 | — |
| Xba I | 2 | 2,5 2,4 |
| Xho I | 0 | — |

2. A plasmid pGA2, isolated from *Corynebacterium glutamicum* LP-6 (deposited under number DSM 5816) characterized by a length of ~19.5 kb and the following restriction cleavage sites:

| Restriction enzymes | Number of cleavage sites | DNA fragment (kb) |
| --- | --- | --- |
| Bam H 1 | 3 | 13,6 4,15 1,75 |
| Eco R I | 2 | 18,5 0.96 |
| Hind III | 5 | 6,61 5,72 3,31 2,04 1,82 |
| Hpa I | 1 | 19,5 |
| Kpn I | 1 | 19,5 |
| Mlu I | 3 | 15,8 2,84 0,82 |
| Sca I | 1 | 19,5 |
| Sma I | 4 | 14,5 3,34 1,00 0,65 |
| Xho I | 0 | — |

3. A recombinant plasmid capable of autonomous replication in coryneform bacteria, comprising the plasmid pGA1 in accordance with claim 1 and at least one foreign DNA fragment.

4. A recombinant plasmid capable of autonomous replication in coryneform bacteria, comprising the plasmid pGA2 in accordance with claim 2 and at least one foreign DNA fragment.

5. A plasmid vector according to claim 3 or 4, comprising:
   a) plasmid pGA1 or pGA2 or of a DNA sequence derived from these plasmids, and
   b) a DNA fragment derived from a vector replicating in *E. coli* which vector carries a resistance gene.

6. Plasmid vector pHS2-1 according to claim 5, consisting of plasmid pGA1 and the *E. coli* vector pHSKm1, characterized by the restriction map of FIG. 4.

7. Plasmid vector pFBH2 according to claim 5, consisting of a DNA sequence from pGA2 and the mobilizable *E. coli* vector pK18::mob, characterized by the restriction map corresponding to FIGS. 5 and 6.

8. Recombinant plasmid according to claim 3 or 4 which further comprises an *E. Coli* expressible in coryneform bacteria.

9. Coryneform bacteria which contain a recombinant plasmid according to claim 3 or 4.

* * * * *